United States Patent [19]

Cinzori et al.

[11] Patent Number: 4,560,874
[45] Date of Patent: Dec. 24, 1985

[54] REFERENCE CHANNEL FOR SENSING OPTICAL CONTAMINATION

[75] Inventors: Robert J. Cinzori, Santa Barbara; Mark T. Kern, Goleta, both of Calif.

[73] Assignee: Santa Barbara Research Center, Goleta, Calif.

[21] Appl. No.: 614,716

[22] Filed: May 29, 1984

Related U.S. Application Data

[62] Division of Ser. No. 269,210, Jun. 2, 1981, abandoned.

[51] Int. Cl.⁴ .............................................. G01J 1/00
[52] U.S. Cl. ................................... 250/339; 250/342
[58] Field of Search .................... 250/338 R, 341, 339, 250/342; 340/567, 600

[56] References Cited

U.S. PATENT DOCUMENTS

| 2,892,378 | 6/1959 | Canada | 252/574 |
|---|---|---|---|
| 3,586,862 | 9/1969 | Topol | 250/574 |
| 3,872,315 | 3/1975 | Boll | 250/575 |
| 3,901,812 | 8/1975 | Hallengren | 250/575 |
| 4,119,949 | 10/1978 | Lindgren | 340/600 |
| 4,188,533 | 2/1980 | Ashenfelter et al. | 250/338 |
| 4,242,669 | 12/1980 | Crick | 250/342 |

FOREIGN PATENT DOCUMENTS

| 156121 | 3/1966 | Fed. Rep. of Germany . |
| 1939867 | 6/1966 | Fed. Rep. of Germany . |
| 2833635 | 2/1980 | Fed. Rep. of Germany . |
| 1395113 | 5/1975 | United Kingdom . |

*Primary Examiner*—Janice A. Howell
*Attorney, Agent, or Firm*—Ronald L. Taylor; Mark J. Meltzer; A. W. Karambelas

[57] ABSTRACT

A simple lightweight apparatus for sensing excessive contamination on the faces of an array of light or infrared detectors comprises mounting a light or infrared-emitting diode near one or more of the detectors. When the diode is energized, the associated detectors should detect its radiation, thereby indicating that the detector is operable and that contamination is not excessive.

4 Claims, 4 Drawing Figures

REFERENCE CHANNEL FOR SENSING OPTICAL CONTAMINATION

This application is a division of application Ser. No. 269,210, filed June 2, 1981, now abandoned.

BACKGROUND OF THE INVENTION

1. Field of the Invention

This invention relates to the field of optical equipment, and more particularly to devices which test the surfaces of optical detectors for contamination that may degrade performance of the detector.

2. Description of the Prior Art

Many different kinds of systems utilize detectors of electromagnetic energy, especially within certain ranges of the electromagnetic spectrum. Detectors that are sensitive to visible light or infrared energy are particularly useful. As an example, a system that senses fires in military vehicles employs two detectors, one capable of detecting energy in the visible spectrum and the other capable of detecting energy in the infrared spectrum. These fire sensor detectors are typically mounted side-by-side in relatively inaccessible locations where dirt, grease, oil, and other contaminants can build up on the detector surfaces. Such contaminants on the detector surfaces reduce the amount of electromagnetic energy reaching the detectors, thereby degrading sensor performance. (In technical literature, the words "detector" and "sensor" are sometimes used synonymously. As used herein, the word "detector" refers to a radiation sensitive element that converts electromagnetic radiation to electrical signals. The word "sensor" refers to a system using at least one "detector", and which includes some other electronics to amplify or process the "detector" signals.)

Built-in test equipment has been used in the past to test for the build-up of contaminants on the face of detector or sensor systems. One such system in the prior art utilizes a protective window having a source of ultraviolet (UV) energy and a detector of ultraviolet energy both located behind the window. Ultraviolet energy is transmitted through the window and reflected back to the ultraviolet detector by a small reflector mounted just outside and to the side of the window.

Another such system in the prior art that tests itself for contaminant build-up utilizes visible spectrum only detectors to perform its sensing function. To perform its self-test, a light bulb mounted outside in front of the detectors is energized to stimulate each of the detectors with an appropriate signal.

In general, when more than one detector is used, such as in these prior art systems, each detector must be equipped with its own built-in test system to test its window for contamination. A possible exception is where the built-in test source—like a light bulb—is so large that it covers several detectors. In most systems, however, it is very undesirable for the test source to be so large since weight and size must be minimized.

While techniques are available to test UV and visible detectors for window contamination, such techniques are not available for infrared detectors. Infrared detectors, per se, often exhibit a broad spectral passband, but they are usually used with a narrow band filter to limit sensitivity to a region of interest. Suitable sources that could be mounted externally thus become impossible to find and automatic monitoring of contamination build-up is no longer feasible. Examination of optical surfaces thus becomes a task of periodic and frequent maintenance.

Since suitable external sources of IR detectors have not been available, internal sources are commonly used. These internal calibration sources (ICS's) are generally placed on the detector side of the filter and often internal to the detector. Using an ICS, no attempt is made to monitor window contamination; its role is solely for the functional testing of the detector and associated electronics.

Previous attempts to overcome this dilemma have generally focused on the test source: finding one that is suitable. Gas and dye lasers are too large and expensive. Lead salt diode lasers are small and compact, but require cryogenic cooling even to generate very small power outputs. Probably the best approach to this problem to date involves using a coil of wire behind an infrared-transmitting window. Even with this approach, however, the source must be moved very close to the detector windows and then pulsed with several amps of current. Thus, compact, directional, low power sources have not been available in the infrared region as they are in the visible and UV regions.

Additionally, it would be desirable if each detector or optical element did not have to be equipped with its own built-in external test source. The more external optical surfaces present, the more likely damage may be sustained in hostile environments. Further, cost and complexity increase very rapidly with the number of external elements present, whereas these factors can be minimized if internal elements can be substituted for external elements.

SUMMARY OF THE INVENTION

The general purpose of this invention is to overcome the above-described problems associated with prior art detector systems by providing a built-in test device that will cause a test failure to be registered when contaminants build up to a predetermined level on the faces of the array of detectors or optical elements, and will do so without significantly blocking the detectors' fields of view.

Another purpose of this invention is to provide a sensor system having a built-in reference channel tester to test for the build-up of contaminants on the face of the detectors or optical elements, and to do so with a minimum of cost and complexity to the overall system.

To accomplish these purposes while overcoming the above disadvantages of the prior art, the present invention provides an apparatus for testing for the presence of a predetermined level of contaminants on the detecting surfaces of a sensor system. This apparatus employs a reference channel for gauging the presence of contamination buildup. As such, it comprises one or more detectors each having one surface which the electromagnetic energy to be detected can strike, an indicator system for indicating when the detector detects electromagnetic energy, and at least one test source of electromagnetic energy disposed near the detecting surfaces of the detectors and oriented so that the test radiation strikes the detecting surfaces. The intensity of the test sources' radiation is calibrated to cause the detectors to detect the test source radiation only when the detecting surfaces have no more than a predetermined arbitrary amount of contamination disposed on them. In most field environments, contaminants tend to build up relatively uniformly on all detectors. Therefore, the sensing of build-up of contamination on the reference channel optical surfaces may be used as a measure of the build-up of contamination on the faces of all other optical surfaces nearby.

Thus, this technique substitutes a reference channel for the multiplicity of external test sources that prior art systems require to perform a test for window contamination. In mechanizing the reference channel, the wavelength of the operation is chosen (1) such that an efficient, compact, low power emitter can be used; and (2) such that contamination build-up will collect at least as rapidly on the reference channel optical surfaces as on other optical surfaces present. Thus the reference channel indicates the worst case contamination present.

While the reference channel is useful as a stand-alone test channel, in a practical system, this technique frequently becomes more useful in conjunction with internal calibration sources (ICS's) in other detector channels.

In a practical system, it is often very advantageous, system-wise, to combine the use of ICS's with a reference channel. Thus, at the same time that the detectors are being tested for functionality, the optical surfaces would be tested for clarity.

Under some circumstances, it may be desirable for the role for the ICS's to be displaced by the reference channel. For example, a very convenient source for a reference channel is a miniature solid-state light emitting diode. These LED's are commercially available in very small housings (0.090 inch diameter) with micro-lenses to concentrate all the emitted light into a narrow field of view (typically 10°). If an optical channel in use by a system just happens to include the wavelength of light emitted by commonly available LED's, it may be advantageous for the reference channel detector to be eliminated and its function taken over by the corresponding system channel on a timeshared basis. In this configuration, that one system channel would not need an ICS since the external LED of the reference channel would provide the stimulus normally provided by the ICS. Thus, the functional test performed by the ICS would instead be performed by the reference channel test source while the reference channel was testing for window contamination.

A method of sensing excessive contamination on the detecting surfaces of a group of detectors comprises the steps of disposing a test source of electromagnetic energy near a detecting surface of a detector, causing the test source to radiate the detecting surface with electromagnetic energy, and determining whether the test source's radiation was detected by the detector.

DETAILED DESCRIPTION OF THE INVENTION

Figure 1:
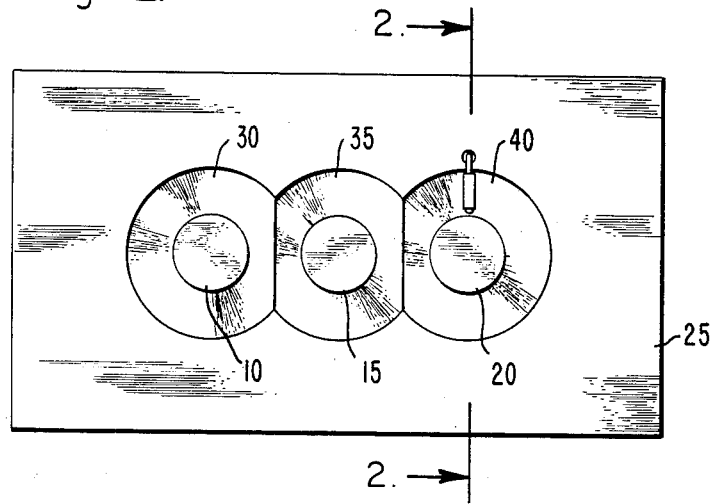
FIG. 1 is a front view of an array of detectors incorporating an embodiment of this invention.
Figure 2:
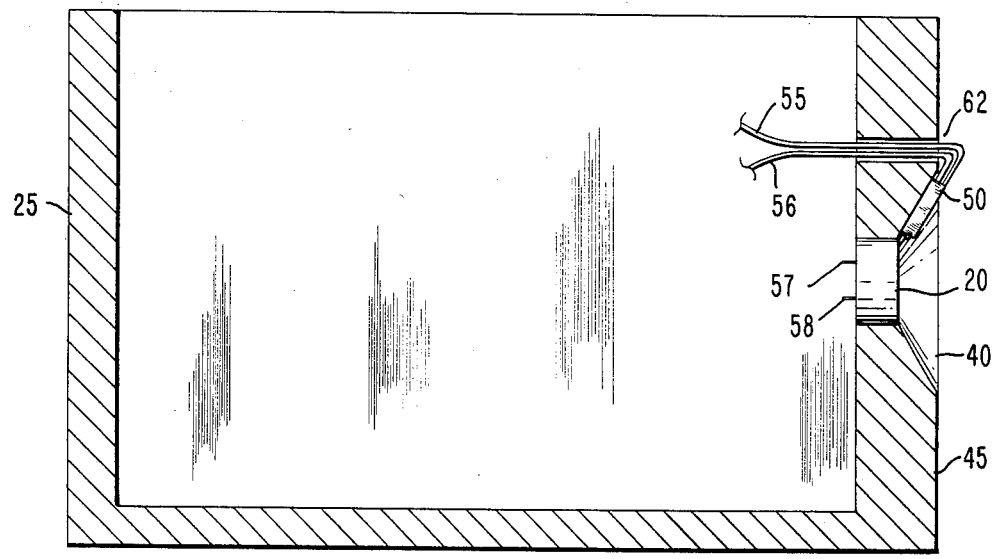
FIG. 2 is a sectional side view of the embodiment shown in FIG. 1.

FIG. 1 shows an array of three detectors 10, 15, and 20 each of which is capable of detecting electromagnetic energy within a certain spectral wavelength band, such as silicon photodiodes. Each detector may be shaped like a disc and have a detecting face which radiant energy may strike. The detectors 10, 15, and 20 are disposed in a wall of a container 25, and are each recessed from the main surface of the container 25. Each detector 10, 15, and 20 also has a beveled surface 30, 35, and 40 respectively around its perimeter. The beveled surface 40 is shown more clearly in FIG. 2. In a preferred embodiment, the beveled surface 40 may be at a 30 degree angle with respect to the front face 45 of the container 25.

Mounted on the beveled surface 40 is a small radiant energy emitting diode 50. In a preferred embodiment, the diode 50 may be an infrared-emitting diode such as the SE1450 manufactured by Spectronics, Inc. The diode 50 may be mounted on beveled surface 40 by attaching the body of the diode 50 to the beveled surface 40, or by any other appropriate means. The diode 50 is oriented such that its energy emitting end is pointed at the detecting face of detector 20. Care must be taken to position the diode 50 close enough to the detector 20 so that the detector 20 will detect radiant energy emitted from the diode 50 when it is energized, but not so close that the diode 50 blocks radiation from the monitored area. The diode 50 has two lead wires 55 and 56 which are passed through a hole 62 in a wall of the container 25. The diode lead wires 55 and 56 are connected to a source of power (not shown) at the appropriate time during an operability test.

The detector 20 has two terminals 57 and 58 which are connected to a test circuit (not shown). The test circuit may be a power source, an amplifier, and either an ammeter or an on-off indicator, all connected in a series circuit. Alternatively, the test circuit may comprise an appropriate electronic processor and an on-off indicator device. When the face of the detector 20 is sufficiently free of contaminants and the diode 50 is energized, the impedance between the terminals 57 and 58 falls and current flowing in the series test circuit displaces the ammeter needle sufficiently or energizes the on-off indicator, thereby indicating that contamination is not excessive. When contamination builds to an excessive level, the impedance between the terminals 57 and 58 does not fall sufficiently when the diode 50 is energized. The current flow in the test circuit will, therefore, be insufficient and the on-off indicator will not turn on.

The above-described embodiment may be modified to incorporate a protective shield, such as glass, in front of the detector 20. Such a shield would be transparent to the electromagnetic energy that the detector was designed to detect, but would physically protect the detector from flying debris or shrapnel in an explosion. Contamination building up on the face of the protective shield would be detected in the manner just described for the case of a detector with no shield.

The embodiment described above represents an application where a single test source is used in the reference channel. For a detector and indicator system, the reference channel time-shares a detector 20 that is used by the system for sensing the presence of explosive fires.

Figure 3:
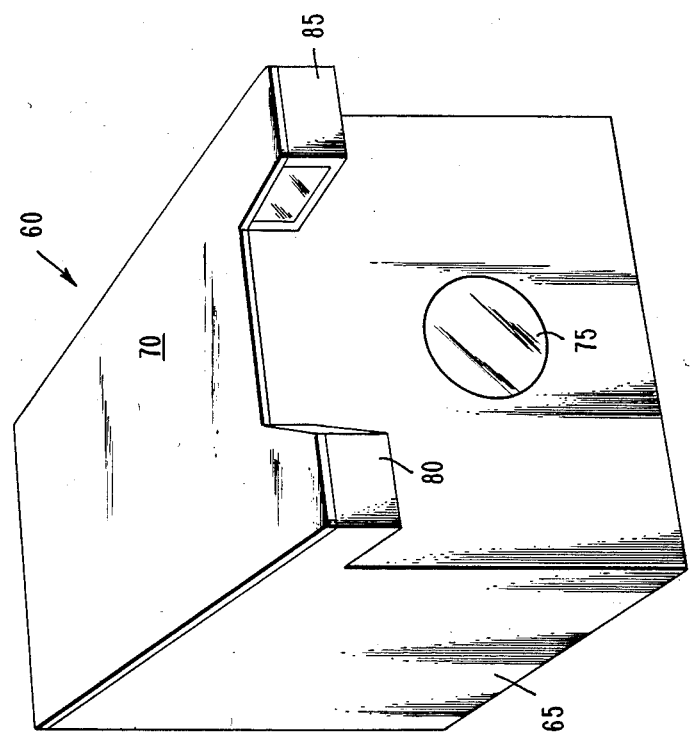
FIG. 3 is an isometric drawing of a single channel long-wavelength heat sensor according to another embodiment of this invention.

Another embodiment of the present invention is shown in FIG. 3. A single-channel long-wavelength heat sensor 60 has a container 65 with a container top 70. The heat sensor 60 has a single detector 75 of long-wavelength electromagnetic energy set in a wall of the container 65. The container has two protrusions 80 and 85 protruding from the container wall in which the detector 75 is set.

Figure 4:
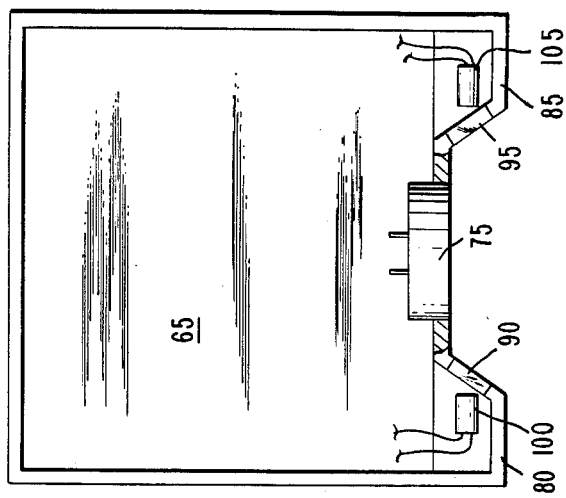
FIG. 4 in a sectional top view showing the detail of the reference channel part of the heat sensor shown in FIG. 3.

The structure of the heat sensor 60 is shown in FIG. 4, which is a top view of the heat sensor 60 with the container top 70 removed. Each protrusion in the container 65 has a window 90 and 95 in the container wall. The windows 90 and 95 are covered with a pane of glass, plastic, or any other suitable transparent material. Behind the window 90 is a test source of electromagnetic energy 100, and behind the window 95 is a test detector of electromagnetic energy 105. The test source 100, the test detector 105 and the windows 90 and 95 are all oriented so that normally the test source 100 will directly irradiate the test detector 105 when the test source 100 is energized. Of course, the test source 100 is chosen to radiate energy of a wavelength that the test detector 105 can detect.

When the environment around the heat sensor 60 is unpolluted, the test detector 105 will detect the radiation of the test source 100 when it is energized by associated test circuitry (not shown). The output of the test detector 105 may be connected to an indicator lamp, a voltmeter, or any other appropriate indicator apparatus that will indicate to a human operator that the test detector 105 is detecting the test source's radiation. The test source may be energized continuously, periodically, or only during random test periods.

If the heat sensor is exposed to contaminated environments, contaminants may begin to build-up on the exposed surfaces of the heat sensor. The build-up of contaminants will generally be uniform over all the exposed surfaces of the heat sensor 60. If contaminants build-up on the windows 80 and 85, less of the radiation from test source 100 will reach and be detected by test detector 105. Depending upon the type of indicating apparatus used, a human operator can be alerted in some way to the presence of an unacceptable amount of contamination on the heat sensor 60. This unacceptable level of contamination would be the maximum amount of contamination that could accumulate on the face of the long-wavelength detector 75, and the sensor circuitry (not shown) that is associated with it, without significantly degrading the performance of the heat sensor system.

The embodiments described above are merely illustrative of the many possible embodiments which can represent applications of the principles of the present invention. Numerous and varied other arrangements can be readily devised in accordance with these principles by those skilled in this art without departing from the spirit and scope of the invention.

What is claimed is:

1. An improved fire sensor system, including a built-in detector window contamination sensing apparatus, said system comprising:
    (a) a long-wavelength infrared radiation detector for detecting electromagnetic radiation in the spectral region of long-wavelength infrared and providing a detector output signal representative thereof;
    (b) an outermost optical surface associated with said long-wavelength detector, said outermost optical surface being subject to obscuration by airborne contaminants;
    (c) a reference channel, located adjacent to said long-wavelength detector, said reference channel including:
        a reference source of electromagnetic radiation having a wavelength shorter than the wavelengths in said long-wavelength infrared spectral region,
        a reference electromagnetic radiation detector for detecting electromagnetic radiation emitted by said reference source,
        an outermost optical surface associated with said reference detector, said outermost optical surface being subject to obscuration by airborne contaminants,
        said reference source located in close proximity to and within the field of view of said reference detector,
        said reference source positioned to direct its electromagnetic radiation substantially towards said reference detector,
        said reference source located external to the outermost optical surface of said reference detector,
        a test circuit for providing an indicator output signal when less than a predetermined amount of electromagnetic radiation is detected by said reference detector;
    whereby said reference source is calibrated to cause said test circuit to provide an indicator output signal when a predetermined degree of contamination is obscuring said reference detector corresponding to similar contamination of the outermost optical surface of said long-wavelength infrared detector.

2. An improved electromagnetic energy detector apparatus according to claim 1 wherein said long-wavelength infrared spectral region is 3–30 micrometers.

3. An improved electromagnetic energy detector apparatus according to claim 2 wherein said reference source emits at a wavelength of approximately 0.9 micrometers.

4. A method of providing a built-in detector window contamination sensing function for an electromagnetic radiation detector apparatus for a fire sensor system, wherein said electromagnetic radiation detector apparatus includes a long-wavelength infrared radiation detector for detecting electromagnetic radiation in the spectral region of long-wavelength infrared, comprising the steps of:
    (a) positioning a reference short-wavelength infrared radiation detector in close proximity to said long-wavelength detector;
    (b) irradiating said reference electromagnetic radiation detector with electromagnetic radiation having a wavelength shorter than the wavelength in said long-wavelength infrared spectral region and of a wavelength detectable by said reference detector;
    (c) providing an indicator output signal when less than a predetermined amount of electromagnetic radiation is detected by said reference detector corresponding to the presence of a predetermined degree of contamination obscuring said reference detector correlating with a similar contaminant caused obscuration of said long-wavelength infrared detector.

* * * * *